(12) United States Patent
Lucas et al.

(10) Patent No.: US 8,742,166 B2
(45) Date of Patent: Jun. 3, 2014

(54) PREPARATION OF POLYISOCYANATES HAVING ISOCYANURATE GROUPS AND THEIR USE

(71) Applicant: BASF SE, Ludwigshafen (DE)

(72) Inventors: Frederic Lucas, Offenburg (DE); Angelika Maria Steinbrecher, Stuttgart (DE); Philippe Desbois, Edingen-Neckarhausen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/889,603

(22) Filed: May 8, 2013

(65) Prior Publication Data

US 2013/0303758 A1    Nov. 14, 2013

Related U.S. Application Data

(60) Provisional application No. 61/643,905, filed on May 8, 2012.

(30) Foreign Application Priority Data

May 8, 2012  (EP) .................................... 12167058

(51) Int. Cl.
*C07C 261/00*  (2006.01)
(52) U.S. Cl.
USPC ........................................................ 560/261

(58) Field of Classification Search
None
See application file for complete search history.

(56) References Cited

U.S. PATENT DOCUMENTS

| 3,862,150 | A | | 1/1975 | Bechara et al. | |
|---|---|---|---|---|---|
| 4,454,317 | A | * | 6/1984 | Disteldorf et al. | 544/193 |
| 5,691,440 | A | | 11/1997 | Katz et al. | |
| 6,703,471 | B2 | * | 3/2004 | Kohlstruk et al. | 528/54 |
| 2005/0080259 | A1 | * | 4/2005 | Revelant et al. | 544/193 |
| 2007/0197759 | A1 | * | 8/2007 | Binder et al. | 528/45 |
| 2010/0022707 | A1 | * | 1/2010 | Schaefer et al. | 524/612 |
| 2012/0288632 | A1 | | 11/2012 | Neu et al. | |

FOREIGN PATENT DOCUMENTS

| DE | 29 16 201 A1 | 10/1980 |
|---|---|---|
| WO | WO 02/092657 A1 | 11/2002 |
| WO | WO 2011/061314 A1 | 5/2011 |

* cited by examiner

Primary Examiner — Karl J Puttlitz
(74) Attorney, Agent, or Firm — Oblon, Spivak, McClelland, Maier & Neustadt, L.L.P.

(57) ABSTRACT

The present invention relates to a novel process for preparing polyisocyanates having isocyanurate groups by a partial trimerization of (cyclo)aliphatic diisocyanates in the presence of at least one trimerization catalyst from the group of ammonium salts of lactames and to the use of the thus obtainable polyisocyanates having isocyanurate groups as a polyisocyanate component in polyurethane coatings.

9 Claims, No Drawings

PREPARATION OF POLYISOCYANATES HAVING ISOCYANURATE GROUPS AND THEIR USE

The present invention relates to a novel process for preparing polyisocyanates having isocyanurate groups by a partial trimerization of (cyclo)aliphatic diisocyanates in the presence of at least one trimerization catalyst from the group of ammonium salts of lactames and to the use of the thus obtainable polyisocyanates having isocyanurate groups as a polyisocyanate component in polyurethane coatings.

Processes for partially or fully trimerizing organic polyisocyanates for preparing polyisocyanates having isocyanurate groups or cellular or compact polyurethanes having isocyanurate groups are known and are described in numerous literature publications.

DE-A 29 16 201 (=U.S. Pat. No. 4,454,317) discloses trimerization catalysts composed of a quaternary, optionally substituted 2-hydroxyethylammonium cation and acids as the anion.

U.S. Pat. No. 3,862,150 discloses salts of tertiary amines and α-substituted carboxylic acids as thermally decomposable catalysts, for example for urethane formation, in which possible α-substituents are nitrile, sulfonyl, sulfuryl, carbonyl, nitro, acetyl and benzoyl groups. The 1,3-dicarbonyl systems or carbonyl-like systems being formed therefrom result in a decarboxylation taking place in a simplified manner, so that such catalysts are readily deactivated, which adversely restricts the temperature range for their usability.

Alkalimetal salts of carboxylic acids are also know as catalysts for trimerization of isocyanates.

However, disadvantages are the presence of water, caused by the preparation from the free acid and an alkali metal hydroxide, in the isocyanate, since it can react with the NCO groups to give carbamic acid groups which, after decarboxylation, form amines which lead in turn to the formation of ureas, undesired because they are usually insoluble.

It is an object of the present invention to provide a catalyst for preparing substantially colorless isocyanurate-containing polyisocyanates by a very simple process in very good quality and reproducibly irrespective of their preparation, which catalyst can be employed over a wide temperature range and which has a uniform structure and a good solubility in the reaction mixture.

This object is achieved by a process for preparing isocyanurate-containing polyisocyanates by at least partly trimerizing (cyclo)aliphatic diisocyanates, in which the reaction is carried out in the presence of at least one trimerization catalyst of salts of tetrasubstituted ammonium cations and anions of lactames.

Preferred ammonium salts are those which are substituted by four hydrocarbon radicals.

Hydrocarbon radicals are substituents which consist exclusively of carbon and hydrogen atoms.

A preferred embodiment of the invention is a process for preparing polyisocyanates having isocyanurate groups by at least partially trimerizing aliphatic or/and cycloaliphatic diisocyanates in the presence of at least one trimerization catalyst and subsequently, if appropriate, deactivating the trimerization catalyst on attainment of the desired degree of trimerization, in which the trimerization catalyst used is at least one tetrasubstituted ammonium lactamates of the formula (I)

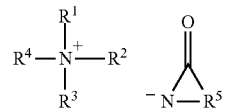

where $R^1$, $R^2$, $R^3$ and $R^4$ may each independently be the same or different and are each a straight-chain or branched optionally substituted, preferably not substituted $C_1$- to $C_{20}$-alkyl group, an optionally substituted, preferably not substituted $C_5$- to $C_{12}$-cycloalkyl group, an optionally substituted, preferably not substituted $C_7$- to $C_{10}$-aralkyl group, or an optionally substituted, preferably not substituted $C_6$-$C_{12}$-aryl group, or two or more of the $R^1$ to $R^4$ radicals together form a 4-, 5- or 6-membered alkylene chain or, together with a nitrogen atom, form a 5- or 6-membered ring which may also contain an additional nitrogen or oxygen atom as a bridge member, or together form a multimembered, preferably six-membered, polycyclic system, preferably bicyclic system, which may also contain one or more additional nitrogen atoms, oxygen atoms or oxygen and nitrogen atoms as bridge members, and $R^5$ may additionally be a divalent $C_1$-$C_{12}$-alkylene, optionally interrupted by one or more oxygen and/or sulfur atoms and/or one or more substituted or unsubstituted imino groups, or substituted by functional groups, aryl, alkyl, aryloxy, alkyloxy, halogen, heteroatoms and/or heterocycles.

In these compounds, a straight-chain or branched, not substituted $C_1$- to $C_{20}$-alkyl group is, for example, methyl, ethyl, propyl, isopropyl, n-butyl, isobutyl, sec-butyl, tert-butyl, pentyl, hexyl, heptyl, octyl, 2-ethylhexyl, 2,4,4-trimethylpentyl, nonyl, dodecyl, eicosyl, decyl, 1,1-dimethylpropyl, 1,1-dimethylbutyl or 1,1,3,3-tetramethylbutyl, an optionally substituted $C_5$- to $C_{12}$-cycloalkyl group is cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, or else a saturated or unsaturated bicyclic system, for example norbornyl or norbornenyl, an optionally substituted $C_7$- to $C_{10}$-aralkyl group is, for example, benzyl, 1-phenylethyl, 2-phenylethyl, α,α-dimethylbenzyl, benzhydryl, p-tolylmethyl, 1-(p-butylphenyl)ethyl, o-, m- or p-chlorobenzyl, 2,4-dichlorobenzyl, o-, m- or p-methoxybenzyl or o-, m- or p-ethoxybenzyl, an optionally substituted $C_6$-$C_{12}$-aryl group is, for example, phenyl, 2-, 3- or 4-methylphenyl, α-naphthyl or β-naphthyl, an optionally substituted $C_1$-$C_{20}$-alkyl optionally interrupted by one or more oxygen and/or sulfur atoms and/or one or more substituted or unsubstituted imino groups or substituted by functional groups, aryl, alkyl, aryloxy, alkyloxy, halogen, heteroatoms and/or heterocycles is, for example, 2-carboxyethyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxy-ethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 1-hydroxy-1,1-di-methylmethyl, 2-hydroxy-2,2-dimethylethyl, 2-phenoxyethyl, 2-phenoxypropyl, 3-phenoxy-propyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, $C_6$- to $C_{12}$-aryl optionally interrupted by one or more oxygen atoms and/or sulfur atoms and/or one or more substituted or unsubstituted imino groups or substituted by functional groups, aryl, alkyl, aryloxy, alkyloxy, halogen, heteroatoms and/or heterocycles, for example tolyl, xylyl, 4-diphenylyl, chlorophenyl, dichlorophenyl, trichlorophenyl, difluorophenyl, methylphenyl, dimethyl-phenyl, trimethylphenyl, ethylphenyl, diethylphenyl, isopropylphenyl, tert-butylphenyl, dodecyl-phenyl, methoxyphenyl, dimethoxyphenyl, ethoxyphenyl, hexyloxyphenyl, methylnaphthyl, iso-propylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitro-phenyl, 4-dimethylaminophenyl, 4-acetylphenyl, methoxyethylphenyl or ethoxymethylphenyl, and divalent $C_1$-$C_{12}$-alkylene, optionally interrupted by one or more oxygen and/or sulfur atoms and/or one or more substituted or unsubstituted imino groups, or substituted by functional groups, aryl, alkyl, aryloxy, alkyloxy, halogen, heteroatoms and/or heterocycles, for example methylene, 1,2-ethylene, 1,3-propylene, 1,3-butylene, 1,4-butylene, 1,5-pentylene, 1,5-hexylene, 1,6-hexylene, 1,8-octylene, 1,10-decylene, 1,12-dodecylene, 2-oxa-1,4-butylene, 3-oxa-1,5-pentylene or 3-oxa-1,5-hexylene.

Examples of $R^1$ to $R^4$ are in each case independently methyl, ethyl, 2-hydroxyethyl, 2-hydroxy-propyl, n-propyl, isopropyl, n-butyl, sec-butyl, tert-butyl, pentyl, hexyl, heptyl, octyl, 2-ethylhexyl, nonyl, decyl, dodecyl, phenyl, α- or β-naphthyl, benzyl, cyclopentyl or cyclohexyl.

When two or more of the $R^1$ to $R^4$ radicals form a ring, these may be, for example, 1,4-butylene, 1,5-pentylene, 3-oxa-1,5-pentylene, 3-aza-1,5-pentylene or 3-methyl-3-aza-1,5-pentylene.

Preferred $R^1$ to $R^4$ radicals are each independently methyl, ethyl, 2-hydroxyethyl, 2-hydroxy-propyl, propyl, isopropyl, n-butyl, tert-butyl, hexyl, octyl, 2-ethylhexyl, nonyl, decyl, dodecyl, phenyl and benzyl, particular preference is given to methyl, ethyl, n-butyl, octyl, decyl, dodecyl, phenyl and benzyl, very particular preference is given to methyl, ethyl, n-butyl, octyl, decyl, dodecyl and in particular methyl, octyl, decyl and dodecyl.

Examples of $R^5$ are methylene, 1,2-ethylene, 1,3-propylene, 1,3-butylene, 1,4-butylene, 1,5-pentylene, 1,5-hexylene, 1,6-hexylene, 1,8-octylene, 1,10-decylene, 1,12-dodecylene, 2-oxa-1,4-butylene, 3-oxa-1,5-pentylene or 3-oxa-1,5-hexylene, preferred are 1,3-propylene, 1,4-butylene, 1,5-pentylene, 1,5-hexylene and 1,12-dodecylene, particular preference is given to 1,5-pentylene.

In one embodiment of the present invention all radicals $R^1$ to $R^4$ are hydrocarbons without any atoms other than carbon or hydrogen.

Examples of such ammonium cations are tetraoctylammonium, tetramethylammonium, tetraethylammonium, tetra-n-butylammonium, trimethylbenzylammonium, triethylbenzylammonium, tri-n-butylbenzylammonium, trimethylethylammonium, trimethyloctylammonium, trimethyldecylammonium, trimethyldodecylammonium, benzyldimethyloctylammonium, benzyldimethyldecylammonium, benzyldimethyldodecylammonium, tri-n-butylethylammonium, triethylmethylammonium, tri-n-butylmethylammonium, diisopropyldiethylammonium, diisopropylethylmethylammonium, diisopropylethylbenzylammonium, N,N-dimethylpiperidinium, N,N-dimethylmorpholinium, N,N-dimethylpiperazinium or N-methyldiazabicyclo[2.2.2]octane. Preferred alkyl-ammonium ions are tetraoctylammonium, tetramethylammonium, tetraethylammonium and tetra-n-butylammonium, particular preference is given to tetramethylammonium and tetraethylammonium and very particular preference is given to tetramethylammonium.

Ammonium ions containing ring systems are, for example, methylated, ethylated or benzylated piperazines, piperidines, morpholines, quinuclidines or triethylenediamines.

In a preferred embodiment the sum of carbon atoms in the radicals $R^1$ to $R^4$ is at least 11, particularly preferred at least 13, very particularly preferred at least 15 and especially at least 17.

In another embodiment of the present invention one radical out of the four radicals $R^1$ to $R^4$ is a substituted $C_1$-$C_{20}$-alkyl the other three radicals being hydrocarbons.

Examples of such ammonium cations are 2-hydroxyethyl trimethylammonium, 2-hydroxypropyl trimethylammonium, 2-hydroxyethyl triethylammonium, 2-hydroxypropyl triethylammonium, 2-hydroxyethyl tri-n-butylammonium, 2-hydroxypropyl tri-n-butylammonium, 2-hydroxyethyl dimethyl benzyl ammonium, 2-hydroxypropyl dimethyl benzyl ammonium, N-(2-hydroxyethyl),N-methyl morpholinium, N-(2-hydroxypropyl),N-methyl morpholinium or 3-hydroxy quinuclidine, preferably 2-hydroxyethyl trimethylammonium, 2-hydroxypropyl trimethylammonium, 2-hydroxyethyl dimethyl benzyl ammonium and 3-hydroxy quinuclidine, very preferably 2-hydroxyethyl trimethylammonium and 2-hydroxypropyl trimethylammonium and particularly preferably 2-hydroxyethyl trimethylammonium.

However, this embodiment is less preferred than the embodiment with all radicals $R^1$ to $R^4$ being hydrocarbons.

Examples of lactames are, for example, γ-butyro lactame, δ-valero lactame, ε-caprolactame, and 6-methyl-ε-caprolactame, preferred are δ-valero lactame and ε-caprolactame and particularly preferred is ε-caprolactame.

In the case of chiral compounds, it is of no importance to the invention which enantiomer or diastereomer is used, or whether the acids are used in racemic form.

The inventive trimerization catalysts are generally thermally stable even at temperatures above 100° C. and are thus catalytically active over a temperature range of from about 30 to 120° C.

However, higher trimerization temperatures, for example above 95° C., are frequently used to trimerize sterically hindered diisocyanates, for example isophorone diisocyanate or 2-butyl-2-ethylpentane 1,5-diisocyanate, and in particular to prepare higher oligomers, since higher space-time yields can thus be achieved. When the inventive catalysts are used the reaction rate of the trimerization reaction can be at least retained or even increased compared to commercial trimerization catalysts, preferably N-(2-hydroxypropyl)-N,N,N-trimethylammonium 2-ethylhexanoate (DABCO TMR® from Air Products). In addition, polyisocyanates having isocyanurate groups and extremely low Hazen color numbers (DIN ISO 6271), for example preferably of less than 40 (for HDI), or below 200, preferably below 100 (for IPDI) are also obtained.

As has already been explained, the trimerization catalysts which can be used in accordance with the invention can be prepared by known processes. To prepare tetrasubstituted ammonium cations, tertiary amines may be reacted with an alkylating agent, for example alkyl halides, dialkyl carbonates or dialkyl sulfates, in the absence or presence of solvents, for example chlorobenzene, toluene or xylene, at temperatures of appropriately from 100 to 180° C. If appropriate, the reaction may be carried out under pressure when the amine used is gaseous under the reaction conditions.

Preferred alkylating agents are methyl chloride, ethyl chloride, methyl iodide, dimethyl carbonate, diethyl carbonate, di-n-butyl carbonate, dimethyl sulfate and diethyl sulfate, and also benzyl chloride.

Examples of suitable tertiary amines include: trimethylamine, triethylamine, tri-n-butylamine, ethyldiisopropylamine, N,N'-dimethylpiperazine, N-methoxyphenylpiperazine, N-methylpiperidine, N-ethylpiperidine, quinuclidine and trialkylamines, for example trimethyl-, triethyl- and tripropylamine, and preferably 1,4-dimethylpiperazine, N,N-dimethylbenzylamine and triethylenediamine.

The tetrasubstituted ammonium ions, obtained after the alkylation, with the alkylating agent as the counterion, for example chloride, iodide, methyl carbonate or methyl sulfate, may then, for example, by treating with an anion exchanger, are then converted in a preferred embodiment to the tetrasubstituted ammonium hydroxide which can then subsequently be reacted with the lactame. The equivalent amounts of water which are formed may either be left in the catalyst or may preferably be removed or depleted by treating with drying agent, for example molecular sieve or zeolite, or azeotropic distillation with an entraining agent, for example cyclohexane, benzene or toluene. In general, a water content in the catalyst of below 0.5% by weight is sufficient for use in the inventive reaction and is aimed for.

The presence of water in the reaction generally leads, as a result of hydrolysis of the isocyanates and decarboxylation of the resulting carbamic acids, to amines which in turn react with isocyanates to give sparingly soluble, undesired ureas.

It is also possible to carry out a direct exchange on an ion exchanger column. To this end, a basic ion exchange resin (for example Amberlyst®, Dowex® or Sephadex® type) is activated with potassium hydroxide solution or sodium hydroxide solution and laden with the desired lactamate. Afterward, the chromatography column is charged with the quaternary ammonium salt and eluted. The eluate contains the desired quaternary ammonium carboxylate. The solvent may be removed by applying vacuum.

In the case of the quaternary ammonium halides, the catalysts can also be obtained in very pure form by cation exchange in solution when the silver carboxylates on which the lactamates are based are used as reaction partners.

The inventive catalysts can be prepared, for example in a similar manner to the working methods, such as in U.S. Pat. No. 5,691,440, col. 11, line 24-col. 12, line 41 or WO 02/092657 A1, page 13, lines 10 to 23.

The alkylation of tertiary amines may be performed, for example, as follows: the tertiary amine, if appropriate in a suitable solvent, for example a $C_1$-$C_4$-alcohol, preferably methanol or ethanol, is reacted with the alkylating agent in super- or substoichiometric or preferably equimolar amounts, for example 0.75-1.25 mol/mol, preferably 0.9-1.1 mol/mol, based on the tertiary amine, if appropriate under elevated pressure, for from 30 minutes to 24 h, at a temperature between room temperature and 120° C., if appropriate at rising temperature in the course of the reaction. On completion of reaction, the volatile constituents are removed by distillation and, if appropriate, washed or recrystallized.

The salt of tetrasubstituted ammonium cation with the anion of the lactame can be prepared, for example, as follows: a commercially available anion of the lactame, preferably an alkali metal salt, particularly preferably a potassium or sodium salt and especially preferably the sodium salt of the lactame in a suitable solvent, for example a $C_1$-$C_8$-alcohol, preferably methanol, ethanol, n-butanol, 2-ethyl hexanol, ethylene glycol or diethylene glycol, is mixed with the ammonium halide in super- or substoichiometric or preferably equimolar amounts, for example 0.9-1.2 mol/mol, preferably 0.95-1.1 mol/mol, and particularly preferably 1-1.05 mol/mol based on the lactame anion. The mixture is stirred until the salt of the halide, usually an alkali metal halide, precipitates usually within 24 hours, preferably within 18 hours and very preferably within 12 hours at a temperature up to 40° C., preferably up to 30° C. and very preferably up to 25° C.

It may be useful to support precipitation by cooling to 10° C. or even 0° C.

The precipitate can be removed by filtration or other means, such as centrifugation or vacuum filtration.

On completion of reaction, the volatile constituents can be removed by distillation and, if appropriate, washed or recrystallized. After any solvent present has been removed together with water present, for example by distillation, if appropriate under reduced pressure, the inventive catalyst can be used and may, if appropriate, be taken up in a solvent. Such a solvent may also contain groups reactive toward isocyanate, e.g. methanol, ethanol, n-butanol, 2-ethyl hexanol, ethylene glycol or diethylene glycol.

Commercially available anions of the lactame often contain significant or even higher amounts of the lactame in its protonated form. The lactame in its protonated form can be separated off by suitable processes or preferably left in the mixture. In the latter case the lactame reacts with the isocyanate groups forming capped isocyanates. As the catalyst is used in minor amounts the formation of capped isocyanate groups usually negligible.

The inventive catalyst may be used in bulk, as solution or as suspension.

When the catalyst is used as the solution, depending on the solubility in the solvent used, a solution having a dilution of generally 10-80%, preferably 10-50%, more preferably 15-45% and most preferably 30-40% by weight is established.

The trimerization catalysts used may also be mixtures with other known trimerization catalysts, and these may be mixed in broad ratios, for example in ratios of from 90:10 to 10:90, preferably from 80:20 to 20:80 and more preferably from 60:40 to 40:60.

To prepare the polyisocyanates having isocyanurate groups, the inventive trimerization catalysts, depending on their catalytic activity, are appropriately used in very small effective amounts which can be determined experimentally in a simple manner.

In general, the tetrasubstituted ammonium lactamates are used in the process according to the invention in an amount of from 0.005 to 0.1% by weight, preferably from 0.01 to 0.05% by weight, based on the weight of the (cyclo)aliphatic diisocyanates.

The process according to the invention is appropriately carried out at a temperature in the range from 10 to 150° C. and reaction times of 10 min to 6 hours, preferably of from 20 min to 3 hours, more preferably of from 20 min to 2 hours. At temperatures above 150° C., discoloration of the polyisocyanates having isocyanurate groups may occur, for example in the case of prolonged reaction times.

When the inventive tetrasubstituted ammonium lactamates are used, preference is given to employing reaction temperatures above 50° C., more preferably from 60 to 120° C., and substantially colorless trimerization products are obtained.

The trimerization may be carried out continuously, semi-continuously or batchwise, preferably batchwise.

In general, it is unimportant which components are initially charged or added. Usually, the isocyanate to be trimerized is at least partly, preferably fully, initially charged and the at least one catalyst is added slowly and/or in portions, then brought to the desired reaction temperature, and the remainder of the catalyst is added, if appropriate in portions.

An alternative preparation variant proceeds as follows: a batchwise process is performed in a stirred reactor. The mixture of diisocyanate and catalyst is initially charged typically at approx. 40° C. Afterward, the trimerization is initiated by increasing the temperature of the reaction mixture to from 50 to 140° C., preferably to from 55 to 100° C. Alternatively, the catalyst may also be metered in after the diisocyanate has attained the temperature necessary for the reaction. The trimerization is generally exothermic, the catalyst can be used in pure form. It is also possible to dissolve the catalyst in a suitable solvent and to use it in this form.

The continuous trimerization is appropriately carried out in a reaction coil with continuous, simultaneous metering of diisocyanate and the catalyst at from 50 to 160° C. and within from 30 seconds to 4 hours. A reaction coil having a small diameter leads to the achievement of high flow rates and consequently good mixing. It is also advantageous to heat the diisocyanate/catalyst mixture to from approx. 50 to 60° C. before entry into the reaction coil. For more precise metering and optimal mixing of the catalyst, it is also advantageous to dissolve the catalyst in a suitable solvent. In principle, suitable solvents are those in which the catalyst has a good solubility. The continuous trimerization may also be carried out in a tank battery. Also conceivable is a combination of tank battery and tubular reactor.

Typically, the reaction is carried out in a gas or gas mixture which is inert under the reaction conditions, for example those having an oxygen content of below 2%, preferably below 1%, more preferably below 0.5% by volume; preference is given to nitrogen, argon, helium, nitrogen-noble gas mixtures; particular preference is given to nitrogen.

Once the desired degree of trimerization, i.e. NCO content, or degree of reaction (based on the NCO content before the reaction) of the isocyanurate/(cyclo)aliphatic diisocyanate reaction mixture has been attained, the degree of reaction appropriately being in the range of from 20 to 45% of the NCO groups, preferably from 25 to 35% of the NCO groups, and for which typically reaction times of from 0.05 to 4 hours, preferably from 10 min to 3 hours, are required, the trimerization reaction may be ended, for example, by deactivating the trimerization catalyst.

In addition to monomeric isocyanate, the product comprises compounds which have one or more isocyanurate structures. Compounds of this type are described in the literature.

Besides polyisocyanates with one or more isocyanurate structures the reaction mixture may contain further polyisocyanates, preferably polyisocyanates comprising one or more uretdione structures. The content of such polyisocyanates is usually from 1 to 15% by weight, preferably from 1 to 5% by weight, based on the total weight of polyisocyanates.

Suitable deactivating agents are, for example, inorganic acids, for example hydrogen chloride, phosphorous acid or phosphoric acid, carbonyl halides, for example acetyl chloride or benzoyl chloride, sulfonic acids or esters, for example methanesulfonic acid, p-toluenesulfonic acid, methyl or ethyl p-toluenesulfonate, m-chloroperbenzoic acid, and preferably dialkyl phosphates, for example di-2-ethylhexyl phosphate and in particular dibutyl phosphate.

In the embodiment in which one of the radicals $R^1$ to $R^4$ is a substituted $C_1$-$C_{20}$-alkyl, deactivating the catalyst by heating to a temperature above e.g. 130° C. is possible, preferably to a temperature above 140° C. and very preferably to a temperature above 150° C.

The deactivating agents may, based on the trimerization catalysts, be used in equivalent or excess amounts, and the smallest effective amount, which can be determined experimentally, is preferred simply for economic reasons. For example, the deactivating agent is used in a ratio to the trimerization catalyst of 1-2.5:1 mol/mol, preferably 1-2:1 mol/mol, more preferably 1-1.5:1 mol/mol and very particularly preferably 1-1.2:1 mol/mol.

The addition depends upon the type of the deactivating agent. For instance, hydrogen chloride is preferably passed over the reaction mixture in gaseous form or preferably passed through the reaction mixture, liquid deactivating agents are usually added in substance or as a solution in a solvent inert under the reaction conditions, and solid deactivating agents in substance or as a solution or suspension in a solvent inert under the reaction conditions.

The deactivating agent is generally added at the reaction temperature, but can also be added at lower temperature.

Preference is given to carrying out the process according to the invention without solvent. However, when the (cyclo) aliphatic diisocyanates are trimerized partially in the presence of solvents or diluents, suitable solvents or diluents for this purpose are either inert and nonpolar or inert and polar, for example toluene, xylene, cyclic ethers, carboxylic esters and ketones or mixtures thereof.

The polyisocyanates having isocyanurate groups which are prepared by the process according to the invention may be freed of any solvent or diluent present and/or preferably of excess, unconverted (cyclo)aliphatic diisocyanates in a manner known per se, for example by thin-film distillation at a temperature of from 100 to 180° C., if appropriate under reduced pressure, if appropriate additionally while passing through inert stripping gas, or extraction, so that the polyisocyanates having isocyanurate groups are obtainable with a content of monomeric diisocyanates of, for example, below 1.0% by weight, preferably below 0.5% by weight, more preferably below 0.3% by weight, even more preferably below 0.2% by weight and in particular not more than 0.1% by weight.

Without removal of the excess monomeric diisocyanates, the polyisocyanates having isocyanurate groups are suitable, for example, for preparing PU foams, cellular or compact elastomers, casting compositions and adhesives. The monomer-free and monomer-containing polyisocyanates having isocyanurate groups may also be modified in a manner known per se by introducing, for example, urethane, allophanate, urea, biuret and/or carbodiimide groups, and/or the isocyanates may be capped with suitable capping agents.

The process according to the invention can be used to trimerize any organic diisocyanates having aliphatic, cycloaliphatic or aliphatic and cycloaliphatic isocyanate groups or mixtures thereof.

Suitable aliphatic diisocyanates have advantageously from 3 to 16 carbon atoms, preferably from 4 to 12 carbon atoms, in the linear or branched alkylene radical, and suitable cycloaliphatic diisocyanates have advantageously from 4 to 18 carbon atoms, preferably from 6 to 15 carbon atoms, in the cycloalkylene radical. Examples include:

1,4-diisocyanatobutane, 2-ethyl-1,4-diisocyanatobutane, 1,5-diisocyanatopentane, 2-methyl-1,5-diisocyanatopentane, 2,2-dimethyl-1,5-diisocyanatopentane, 2-propyl-2-ethyl-1,5-diisocyanato-pentane, 2-butyl-2-ethyl-1,5-diisocyanatopentane, 2-alkoxymethylene-1,5-diisocyanatopentane, 3-methyl-, 3-ethyl-1,5-diisocyanatopentane, hexamethylene 1,6-diisocyanate, 2,4,4- or 2,2,4-tri-methylhexamethylene 1,6-diisocyanate, 1,7-diisocyanatoheptane, 1,8-diisocyanatooctane, 1,10-diisocyanatodecane, 1,12-diisocyanatododecane, 4,4'-diisocyanatodicyclohexylmethane, 2,4'-diisocyanatodicyclohexylmethane, and also mixtures of the diisocyanatodicyclohexylmethane isomers, 1,3-diisocyanatocyclohexane and also isomer mixtures of diisocyanatocyclohexanes and 1-isocyanato-3-isocyanatomethyl-3,5,5-trimethylcyclohexane. The (cyclo)aliphatic diisocyanates used are preferably hexamethylene 1,6-diisocyanate, isomeric aliphatic diisocyanates having 6 carbon atoms in the alkylene radical and mixtures thereof, 2-butyl-2-ethyl-1,5-di-isocyanatopentane and 1-isocyanato-3-isocyanatomethyl-3,5,5-trimethylcyclohexane, 4,4'-diisocyanatodicyclohexylmethane, 2,4'-diisocyanatodicyclohexylmethane, and also mixtures of the diisocyanatodicyclohexylmethane isomers; particular preference is given to hexamethylene 1,6-diisocyanate and 1-isocyanato-3-isocyanatomethyl-3,5,5-trimethylcyclohexane and mixtures thereof, for example in a ratio of 10:90-90:10, preferably 20:80-80:20 and more preferably 33:67-67:33.

It will be appreciated that the inventive catalysts also catalyze the trimerization of aromatic isocyanates, but are preferred for (cyclo)aliphatic isocyanates.

The inventive novel trimerization catalysts may be used for the trimerization of (cyclo)aliphatic diisocyanates prepared by any processes, for example by a phosgene-free process route or one proceeding with the use of phosgene.

The (cyclo)aliphatic diisocyanates which can be used in accordance with the invention may be prepared by any processes, for example by phosgenating the appropriate diamines and thermally dissociating the dicarbamoyl chlorides formed as an intermediate. (Cyclo)aliphatic diisocyanates prepared by phosgene-free processes do not contain any chlorine compounds as by-products and therefore contain, as a result of the preparation, a fundamentally different by-product spectrum.

It will be appreciated that mixtures of isocyanates which have been prepared by the phosgene process and by phosgene-free processes may also be used.

It has been found that the trimerization catalysts which can be used in accordance with the invention have good catalytic activity in the trimerization of (cyclo)aliphatic diisocyanates, even those prepared by the phosgene process, and result in polyisocyanates having isocyanurate groups which have a low color number.

The (cyclo)aliphatic diisocyanates which can be used in the process according to the invention and are obtainable by a phosgene-free process and especially by thermal dissociation of (cyclo)aliphatic dicarbamic esters are not restricted, and preference is given in particular to selecting diisocyanates obtainable by thermal dissociation of (cyclo)aliphatic dicarbamic esters from the group of hexamethylene 1,6-diisocyanate, 2-butyl-2-ethylpentamethylene 1,5-diisocyanate and 1-isocyanato-3-isocyanatomethyl-3,5,5-trimethylcyclohexane.

In a preferred embodiment of the invention, isocyanates are used which have a total chlorine content of 100 ppm by weight or less, preferably 80 ppm by weight or less.

Polyisocyanates having isocyanurate groups and prepared by these process variants are suitable preferentially for producing polyurethane coatings, for example textile and leather coatings, for polyurethane dispersions and adhesives, and find use in particular as a polyisocyanate component in one- and two-component polyurethane systems for high-grade, weather-resistant polyurethane coatings and high-solids coatings. ppm and percentage data used in this document relate, unless stated otherwise, to percentages by weight and ppm by weight.

The examples which follow are intended to illustrate the invention, but not restrict it to these examples.

EXAMPLES

Catalyst 1:
Mixture of caprolactame (82 wt %) and sodium caprolactamate (18 wt %) (Brüggolen C10, obtainable from Brueggeman).

Catalyst 2:
15.00 g Brüggolen C10 were dissolved in 15.00 g methanol at room temperature.

8.06 g tetraoctylammonium chloride (Aliquat® 336 of Cognis, now BASF) were dissolved in 8 g methanol. The two clear solutions were mixed in a three neck flask at room temperature and stirred. The temperature did not rise.

After 5 minutes a white solid of sodium chloride precipitated. The solution was stored in a fridge for 24 hours.

After filtration a 30 wt % solution of trioctylammonium caprolactamate together with a residual content of caprolactame was obtained.

Catalyst 3:
15.00 g Brüggolen C10 were dissolved in 15.00 g methanol at room temperature.

5.26 g dodecyltrimethylammonium chloride were dissolved in 5.3 g methanol. The two clear solutions were mixed in a three neck flask at room temperature and stirred. The temperature did not rise.

After 5 minutes a white solid of sodium chloride precipitated. The solution was stored in a fridge for 24 hours.

After filtration a 25 wt % solution of dodecyltrimethylammonium caprolactamate together with a residual content of caprolactame was obtained.

Polyisocyanate 1:
400 g (2.98 mol) of hexamethylene diisocyanate (HDI) were placed into a three neck flask equipped with stirrer, thermometer and reflux condenser at 80° C. and 0.48 ml of catalyst 2 were added. Within 7 hours at 80° C. the NCO content dropped to 40.4%.

The reaction was stopped by adding 0.25 ml of a solution of bis-(2-ethylhexylphosphate). The reaction mixture was purified from monomeric HDI by thin film distillation at 5 mbar at at temperature of 165° C.

106 g of a mixture of isocyanurate and uretdione of HDI was obtained with an NCO content of 21.9% and a viscosity of 2800 mPas.

Polyisocyanate 2:
900 g (5.35 mol) of hexamethylene diisocyanate (HDI) were placed into a three neck flask equipped with stirrer, thermometer and reflux condenser at 80° C. and 0.9 ml of catalyst 3 were added. Within 3 hours at 60° C. the NCO content dropped to 39.2%.

The reaction was stopped by adding 0.75 ml of a solution of bis-(2-ethylhexylphosphate). The reaction mixture was purified from monomeric HDI by thin film distillation at 5 mbar at at temperature of 165° C.

186 g of a mixture of isocyanurate and uretdione of HDI was obtained with an NCO content of 22.6% and a viscosity of 1400 mPas.

COMPARATIVE EXAMPLE 168 g (1.00 mol) of hexamethylene diisocyanate (HDI) were placed into a three neck flask equipped with stirrer, thermometer and reflux condenser at 80° C. and 0.05 g of catalyst 1 (Brüggolen C10) were added. On addition of catalyst 1 the reaction mixture became turbid. Within 7 hours the NCO content dropped from 50% to 49.6%, so that little of no reaction as taken place.

The invention claimed is:

1. A process for preparing an isocyanurate-comprising polyisocyanate, the process comprising:
   at least partly trimerizing at least one (cyclo)aliphatic diisocyanate in the presence of at least one trimerization catalyst comprising a salt, which comprises a tetrasubstituted ammonium cation and an anion of a lactam, wherein
   the at least one trimerization catalyst is a tetrasubstituted ammonium lactamate of formula (I):

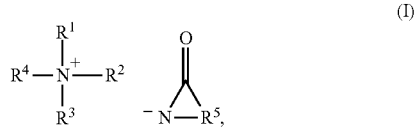

$R^1$, $R^2$, $R^3$ and $R^4$ each independently represent a straight-chain or branched optionally substituted $C_1$- to $C_{20}$-alkyl group, an optionally substituted $C_5$- to $C_{12}$-cycloalkyl group, an optionally substituted $C_7$- to $C_{10}$-aralkyl group, or an optionally substituted $C_6$-$C_{12}$-aryl group, or
   two or more of $R^1$ to $R^4$ radicals together form a 4-, 5- or 6-membered alkylene chain or, together with nitrogen, form a 5- or 6-membered ring optionally comprising additional nitrogen or oxygen as a bridge member, or together form a multi-membered polycyclic system optionally comprising additional nitrogen, oxygen, or any combination thereof as a bridge member or bridge members; and
   $R^5$ represents a divalent $C_1$-$C_{12}$-alkylene, optionally interrupted by oxygen, sulfur, a substituted or an unsubstituted imino group, or any combination thereof, or substituted by a functional group, an aryl group, an alkyl group, an aryloxy group, an alkyloxy group, a halogen, a heteroatom, a heterocycle, or any combination thereof.

2. The process according to claim 1, wherein the $R^1$ to $R^4$ radicals are independently selected from the group consisting of methyl, ethyl, 2-hydroxyethyl, 2-hydroxypropyl, n-propyl, isopropyl, n-butyl, sec-butyl, tert-butyl, pentyl, hexyl, heptyl, octyl, 2-ethylhexyl, nonyl, decyl, dodecyl, phenyl, α- or β-naphthyl, benzyl, cyclopentyl and cyclohexyl.

3. The process according to claim 1, wherein a sum of carbon atoms in the $R^1$ to $R^4$ radicals is at least 11.

4. The process according to claim 1, wherein $R^5$ is selected from the group consisting of methylene, 1,2-ethylene, 1,3-propylene, 1,3-butylene, 1,4-butylene, 1,5-pentylene, 1,5-hexylene, 1,6-hexylene, 1,8-octylene, 1,10-decylene, 1,12-dodecylene, 2-oxa-1,4-butylene, 3-oxa-1,5-pentylene and 3-oxa-1,5-hexylene.

5. The process according to claim 1, wherein the tetrasubstituted ammonium cation is selected from the group consisting of tetraoctylammonium, tetramethylammonium, tetraethylammonium, tetra-n-butylammonium, trimethylbenzylammonium, triethylbenzylammo-nium, tri-n-butylbenzylammonium, trimethylethylammonium, trimethyloctylammonium, trimethyldecylammonium, trimethyldodecylammonium, benzyldimethyloctylammonium, benzyldimethyldecylammonium, benzyldimethyldodecylammonium, tri-n-butyl-ethylammonium, triethylmethylammonium, tri-n-butylmethylammonium, diisopropyl-diethylammonium, diisopropylethylmethylammonium, diisopropylethylbenzylammonium, N,N-dimethylpiperidinium, N,N-dimethylmorpholinium, N,N-dimethylpiperazinium and N-methyldiazabi-cyclo[2.2.2]octane.

6. The process according to claim 1, wherein the tetrasubstituted ammonium cation is selected from the group consisting of 2-hydroxyethyl trimethylammonium, 2-hydroxypropyl trimethylammonium, 2-hydroxyethyl triethylammonium, 2-hydroxypropyl triethylammonium, 2-hydroxyethyl tri-n-butylammonium, 2-hydroxypropyl tri-n-butylammonium, 2-hydroxyethyl dimethyl benzyl ammonium, 2-hydroxypropyl dimethyl benzyl ammonium, N-(2-hydroxy-ethyl),N-methyl morpholinium, N-(2-hydroxypropyl),N-methyl morpholinium and 3-hydroxy quinuclidine.

7. The process according to claim 1, wherein the lactam is selected from the group consisting of γ-butyro lactam, δ-valero lactam, ε-caprolactam, and 6-methyl-ε-caprolactam.

8. The process according to claim 1, wherein the at least one (cyclo)aliphatic diisocyanate is selected from the group consisting of hexamethylene 1,6-diisocyanate, 2-butyl-2-ethyl- 1,5-diisocyanatopentane, 1 -isocyanato-3 -isocyanatomethyl-3,5,5 -trimethylcyclo-hexane, 4,4'-diisocyanatodicyclohexylmethane, 2,4'-diisocyanato-dicyclohexylmethane, and a mixture of diisocyanatodicyclohexylmethane isomers.

9. The process according to claim 1, further comprising:
   deactivating the at least one trimerization catalyst with a deactivating agent after a desired degree of trimerization of the at least one (cyclo)aliphatic diisocyanate has been attained.

* * * * *